(12) United States Patent
Okiyama

(10) Patent No.: US 8,231,596 B2
(45) Date of Patent: Jul. 31, 2012

(54) COMMUNICATING MEMBER, MEDICAL CONTAINER USING THE SAME, AND INFUSION PREPARATION TOOL SET

(75) Inventor: Tadashi Okiyama, Hiroshima (JP)

(73) Assignee: JMS Co., Ltd., Hiroshima (JP)

( * ) Notice: Subject to any disclaimer, the term of this patent is extended or adjusted under 35 U.S.C. 154(b) by 972 days.

(21) Appl. No.: 12/225,833

(22) PCT Filed: Mar. 28, 2007

(86) PCT No.: PCT/JP2007/056628
§ 371 (c)(1),
(2), (4) Date: Sep. 30, 2008

(87) PCT Pub. No.: WO2007/114157
PCT Pub. Date: Oct. 11, 2007

(65) Prior Publication Data
US 2009/0143758 A1    Jun. 4, 2009

(30) Foreign Application Priority Data
Mar. 31, 2006  (JP) ................................. 2006-097801

(51) Int. Cl.
*A61B 19/00*    (2006.01)
*A61M 5/32*    (2006.01)
(52) U.S. Cl. ........................................ 604/408; 604/403
(58) Field of Classification Search ........... 604/403–416
See application file for complete search history.

(56) References Cited

U.S. PATENT DOCUMENTS

| 4,479,989 | A | 10/1984 | Mahal | |
| 5,364,384 | A * | 11/1994 | Grabenkort et al. | 604/408 |
| 6,162,206 | A * | 12/2000 | Bindokas et al. | 604/533 |
| 7,530,974 | B2 * | 5/2009 | Domkowski et al. | 604/415 |
| 2006/0137763 | A1 * | 6/2006 | Hogan et al. | 141/329 |

FOREIGN PATENT DOCUMENTS

| EP | 1 658 871 | 5/2006 |
| JP | 4-35666 | 2/1992 |
| JP | 4-37437 | 3/1992 |
| JP | 5-228201 | 9/1993 |
| JP | 63-35257 | 2/1998 |
| JP | 2004-208883 | 7/2004 |

* cited by examiner

*Primary Examiner* — Tatyana Zalukaeva
*Assistant Examiner* — Philip R Wiest
(74) *Attorney, Agent, or Firm* — Hamre, Schumann, Mueller & Larson, P.C.

(57) ABSTRACT

A communicating member for a medical container contains a plate member 4 having a first opening 5 and a second opening 6, a first connection port 15 including the first opening 5, a plug 9 that obturates the first opening 5 and a first approximately cylindrical member 19 that is in communication with the first opening 5, a second connection port 16 including the second opening 6 and a barrier member 13 that obturates the second opening 6, and a continuous wall 17 disposed on the plate member 4 on the first approximately cylindrical member 19 side and disposed upright on the plate member 4 such that the continuous wall 17 encloses the first opening 5 and the second opening 6 when the plate member is viewed from above; and the first approximately cylindrical member 19 is provided with a first communication part 20 that has an opening on the second opening 6 side.

15 Claims, 16 Drawing Sheets

COMMUNICATING MEMBER, MEDICAL CONTAINER USING THE SAME, AND INFUSION PREPARATION TOOL SET

TECHNICAL FIELD

The present invention relates to a communicating member that constitutes a medical container that can store fluid such as medicinal fluid, high-calorie infusion fluid or the like, a medical container using this communicating member, and an infusion preparation tool set containing the medical container and a fluid-sending route connected to the medical container.

BACKGROUND ART

Examples of medical containers include a medical container for storing a medicinal fluid for an intravenous drip, a medical container for storing a nutritional supplement (also called "high-calorie infusion fluid") supplied to the central vein, a medical container for storing nutrients that are supplied to the digestive tract through a catheter inserted via a nostril (also called "enteral nutrition"), etc. Such medical containers are composed of a main container unit made of a flexible sheet and are provided with connection ports such as a fluid discharge port, a mixed injection port and the like that are fixed to the main container unit. The fluid discharge port is provided to discharge the medicinal fluid or the like present in the main container unit out of the main container unit, and the mixed injection port is provided to add a minor component such as insulin or the like to the infusion fluid or the like present in the main container unit (for example, see Patent Documents 1 and 2).

The connection ports such as the fluid discharge port, the mixed injection port and the like are all composed of pipes that are firmly secured to the main container unit by being sandwiched by a flexible sheet that constitutes the main container unit, sealing members that seal the distal ends of the pipes located outside the main container unit, and other like components. Materials for use as the sealing members are synthetic rubber, thermoplastic elastomer, etc., into which a metal injection needle, a resin introducer needle or the like can be inserted. The pipes are relatively-hard molded products made of plastic. In addition, the aforementioned pipes have the shape of a long and narrow cylinder so that the sheet that constitutes the main container unit is not pierced by the tip of the injection needle, introducer needle or the like when the injection needle, introducer needle or the like is inserted into the sealing member.

The aforementioned high-calorie infusion fluid is a nutrient preparation containing amino acid, sugar, lipid, vitamin, etc. These ingredients are stored separately, for example, in vials and mixed in a medical container immediately before administration into a patient, thereby being formed into high-calorie infusion fluid. As disclosed in Patent Document 2 for example, each ingredient flows into an empty medical container through a flexible tube to be mixed with each other. When air bubbles are present in the high-calorie infusion fluid thus prepared, there is a possibility that air bubbles flow into the patient side upon administration, and this is dangerous. Therefore, prior to administration, vibrations are given to the medical container, or the medical container is turned upside down, so as to carry out vapor-liquid separation as much as possible.

Patent document 1: JP 2004-208883 A

Patent document 2: JP H5-228201 A

DISCLOSURE OF INVENTION

Problem to be Solved by the Invention

However, the pipes that constitute the aforementioned connection ports have the shape of a long and narrow cylinder as described above. Therefore, once air bubbles enter the space inside the connection ports, it is not easy to remove the air bubbles from the space. Moreover, if air bubbles enter the space inside the mixed injection port, the air bubbles may function as a bung and the small amount of medicinal fluid concomitantly introduced through the mixed injection port cannot be diffused. Such a problem is not limited only to a medical container that stores high-calorie infusion fluid, but it is common among medical containers that use long and narrow tubes that are for use as part of connection ports.

The present invention provides a communicating member provided with connection ports that can prevent damage to a main container unit that may be caused by an injection needle or the like and that can prevent the retention of air bubbles; a medical container using this communicating member; and an infusion preparation tool set.

Means for Solving Problem

It is a feature of the communicating member of the present invention that the communicating member is for use with a medical container and can bring the inside and outside of a main container unit into communication while being fixed to the main container unit composed of a flexible sheet; and the communicating member includes a plate member that has a first opening and a second opening, a first connection port including the first opening, a plug that obturates the first opening, a first approximately cylindrical member that is in communication with the first opening, a second connection port including the second opening and a barrier member that obturates the second opening, and a continuous wall that is disposed on the plate member on the first approximately cylindrical member side and disposed upright on the plate member as if enclosing the first opening and the second opening when the plate member is viewed from above; and the first approximately cylindrical member is provided with a first communication portion that has an opening on the second opening side.

The medical container of the present invention is characterized in being provided with a main container unit composed of a flexible sheet and the communicating member of the present invention that is fixed to the main container unit and that brings the inside and outside of the main container unit into communication.

The infusion preparation tool set of the present invention is characterized in including the medical container of the present invention and a fluid-sending route that can be connected to the second connection port. The fluid-sending route includes a fluid sending tube; a connecting means that is disposed at one end of the fluid-sending tube, that allows a communicating path that brings the inside of the main container unit and the fluid-sending tube into communication to be formed therein, and that can maintain the state of the communicating path being formed; and a needle disposed in the other end of the fluid-sending tube.

BEST MODE FOR CARRYING OUT THE INVENTION

Figure 1:
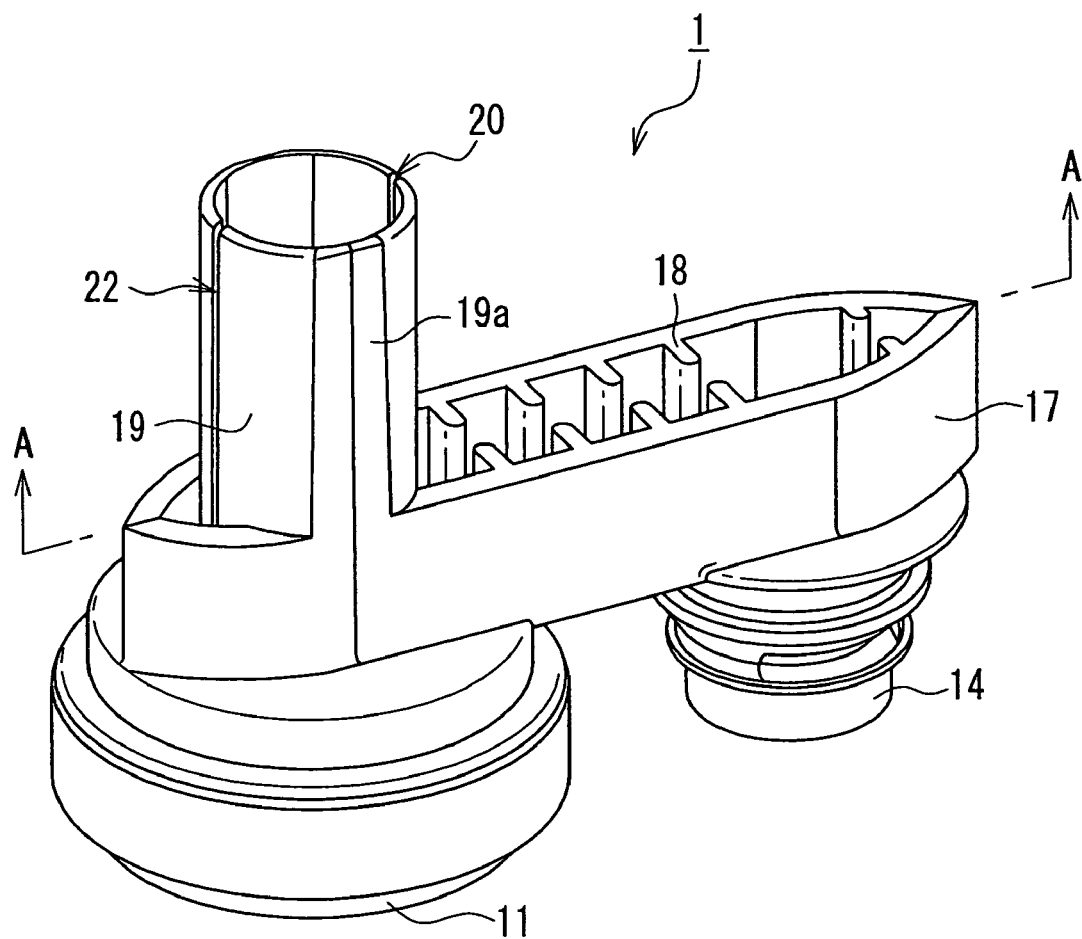
FIG. 1 is a perspective view of an example of the communicating member of the present invention.

It is preferable that in the communicating member of the present invention the first connection port is provided with a first pedestal that is disposed upright on the plate member so as to be in communication with the first opening. In this case, the plug is disposed in the tip portion of the first pedestal and obturates the first pedestal. In this configuration also, although indirectly, the first opening is obturated by the plug. The first pedestal is, for example, tubular or annular.

It is preferable that in the communicating member of the present invention the second connection port is provided with a second pedestal disposed upright on the plate member so as to be in communication with the second opening. In this case, a barrier member is provided in the tip portion of the second pedestal and obturates the second pedestal. In this configuration also, although indirectly, the second opening is obturated by the barrier member. The second pedestal is, for example, tubular or annular.

It is preferable that the first communicating portion is disposed at least in the base portion of the first approximately cylindrical member.

The first communicating portion may be formed by, for example, providing a through-hole penetrating the cylindrical wall of the first approximately cylindrical member in the thickness direction, or may be formed by providing a slit in the cylindrical wall of the first approximately cylindrical member along the longitudinal direction of the first approximately cylindrical member.

It is preferable that the first communicating portion is provided such that the first communicating portion overlaps part of a line connecting the center of the plug and the center of the barrier member when the communicating member is viewed from above such that the inner space of the first approximately cylindrical member can be seen.

The first approximately cylindrical member may further be provided with a second communicating portion that has an opening on the side opposite the second opening.

The communicating member of the present invention preferably is provided with a plurality of reinforcing ribs that are disposed upright on the inner surface of the continuous wall and are formed integral with the plate member.

The barrier member is preferably, for example, a disc-like valve having a slit. It is preferable that a male luer having a 6/100 tapered surface as defined by ISO594-1 or ISO 594-2 can be inserted into the slit.

It is preferable that the second connection port further is provided with a covering member that supports the barrier member, and the periphery of the surface of the barrier member is covered with the covering member. In this case, the barrier member is secured firmly to the second pedestal.

The second connection port further may include a second approximately cylindrical member disposed upright on the plate member so as to be in communication with the second opening. In this case, it is preferable that the second approximately cylindrical member is provided with a third communicating portion that has an opening on the first opening side.

In the infusion preparation tool set of the present invention, it is preferable that the barrier member of the communicating member is a disc-like valve having a slit. In this case, it is preferable that the tip portion of the connecting means can be inserted into the slit of the barrier member and the base portion thereof includes a conduit portion connected to the fluid-sending tube.

In a preferable example of the infusion preparation tool set of the present invention, the connecting means includes a lock connector provided with the aforementioned conduit portion and a pair of locking levers. The locking levers are connected to both lateral sides of the conduit portion and extend along the axial direction of the conduit portion. A locking claw that projects inward is provided at the tip of each locking lever. In this case, it is preferable that the communicating member is provided with a covering member that supports the barrier member, the periphery of the surface of the barrier member is covered with the covering member, and the covering member is provided with a first protrusion and a second protrusion in this order when counted from the tip side that can be engaged with the locking claws of the locking levers. Thus, by positioning the tip of the conduit portion of the lock connector to face the barrier member, a first connected state in which the locking claws of the locking levers are engaged with the first protrusion, and a second connected state in which the locking claws of the locking levers are engaged with the second protrusion, can be attained. In the second connected state, the connection of the lock connector with the covering member is maintained such that the tip portion of the conduit portion inserted into the slit of the barrier member is kept in a position where the tip portion serves as a communicating path that brings the inside of the main container unit and the fluid-sending route into communication. In the first connected state, the connection of the lock connector with the covering member is maintained such that the tip portion of the conduit portion of the locking connector is kept in a position where the tip portion is not in the slit of the barrier member, or in a position where the tip portion is shallowly inserted into the slit compared with the second connected state.

In an example of the infusion preparation tool set of the present invention, the second connection port is disposed closer to the base portion than the second protrusion and has a portion with a reduced diameter on the second pedestal side of the plate member. In this case, it is preferable that the example of the infusion preparation tool set of the present invention is provided with a position regulator that is installed on the reduced diameter portion when the locking claws of the locking levers are in the state of engagement with the first protrusion and that prevents the connecting means from moving into the second connected state.

The position regulator is, for example, a c-clip, i.e., a ring-shaped stopper with a gap.

Next, the present invention shall be described in detail with reference to the drawings.

(Embodiment 1)

In Embodiment 1, an example of the communicating member of the present invention and an example of a medical container in which the communicating member is used are described.

Figure 2:
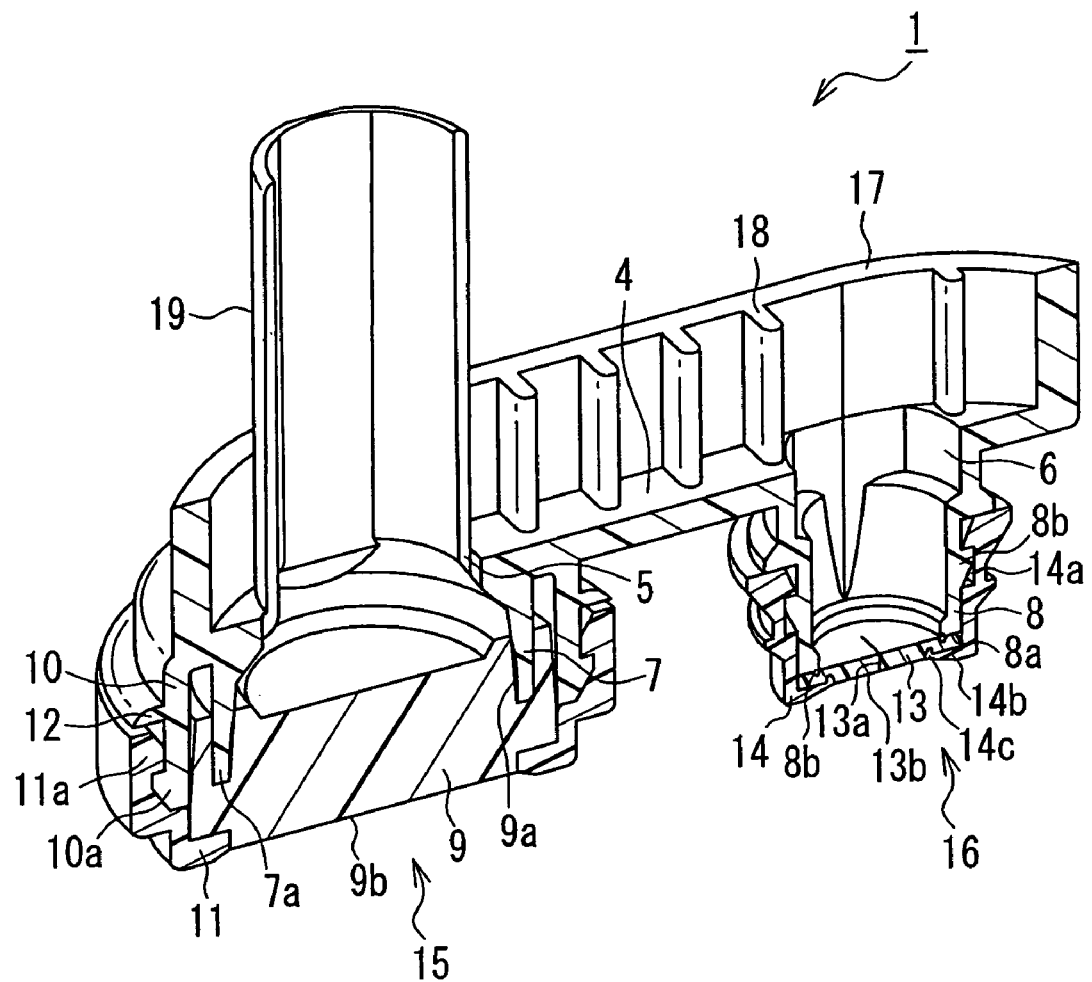
FIG. 2 is a cross-sectional view taken along the line A-A of the communicating member shown in FIG. 1.
Figure 3:
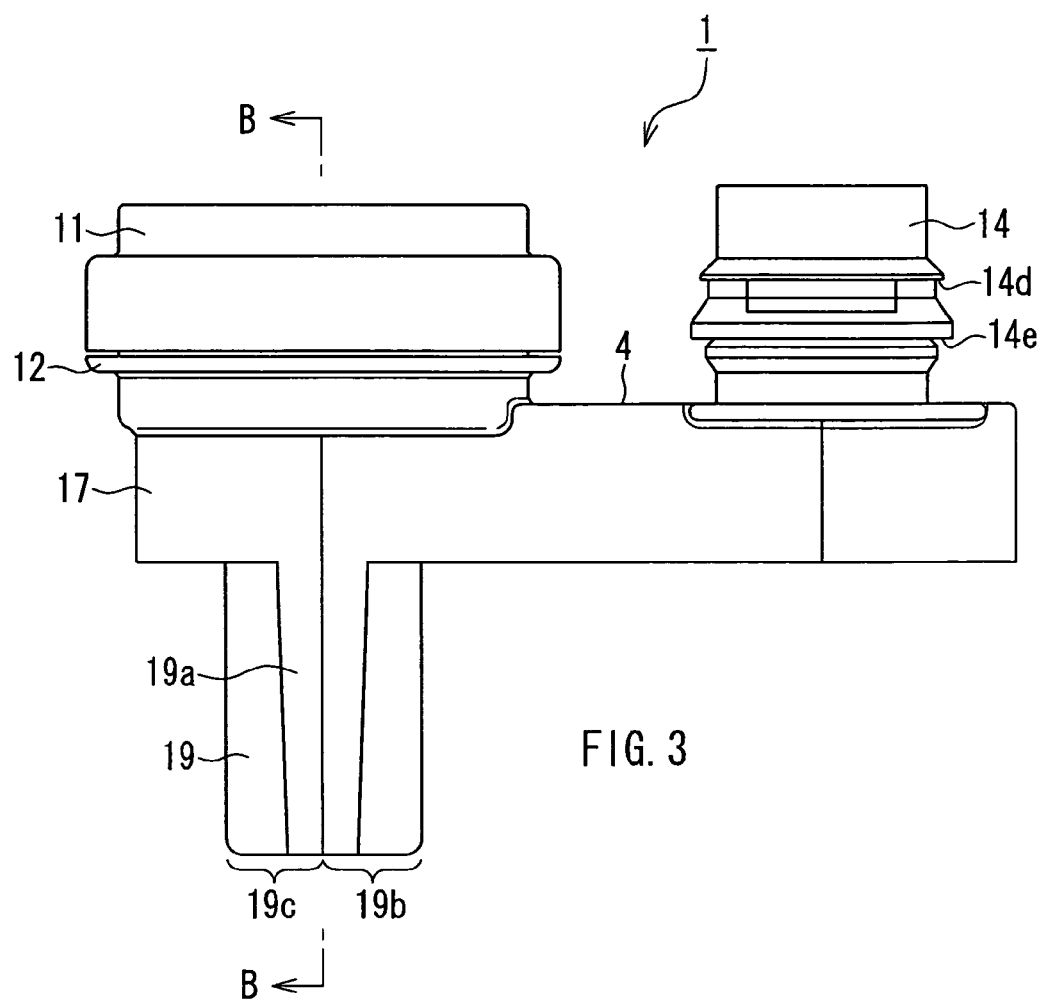
FIG. 3 is a front view of the communicating member shown in FIG. 1.
Figure 4:
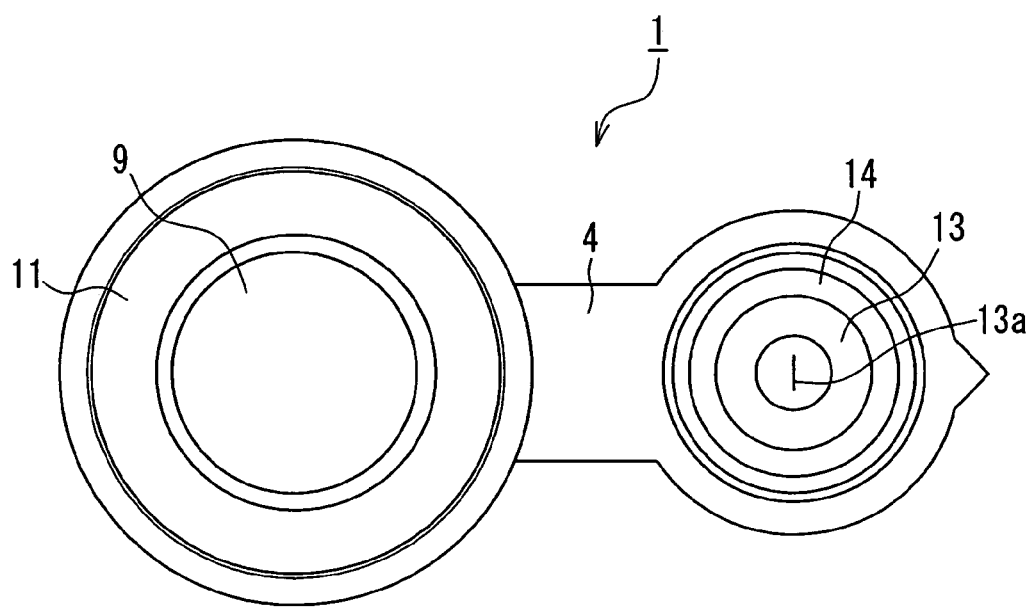
FIG. 4 is a plan view of the communicating member shown in FIG. 1.
Figure 5:
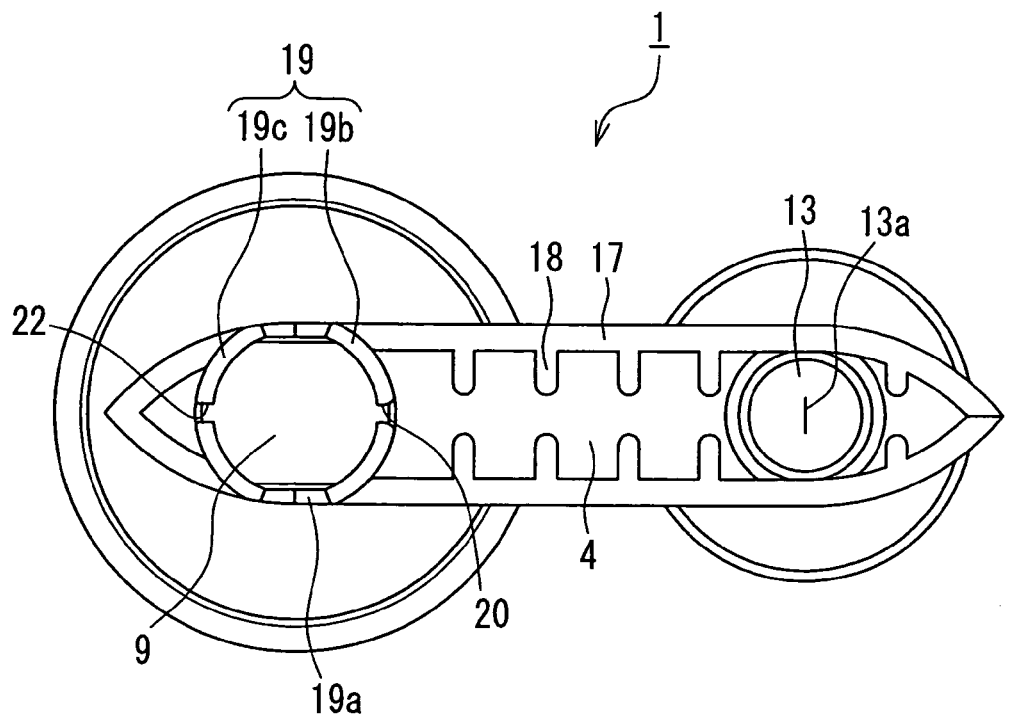
FIG. 5 is an underside view of the communicating member shown in FIG. 1.
Figure 6:
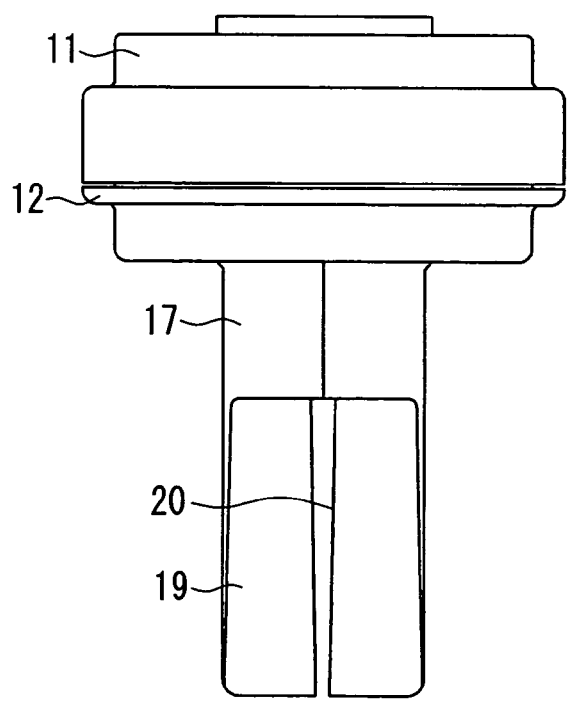
FIG. 6 is a side view of the communicating member shown in FIG. 1.
Figure 7:
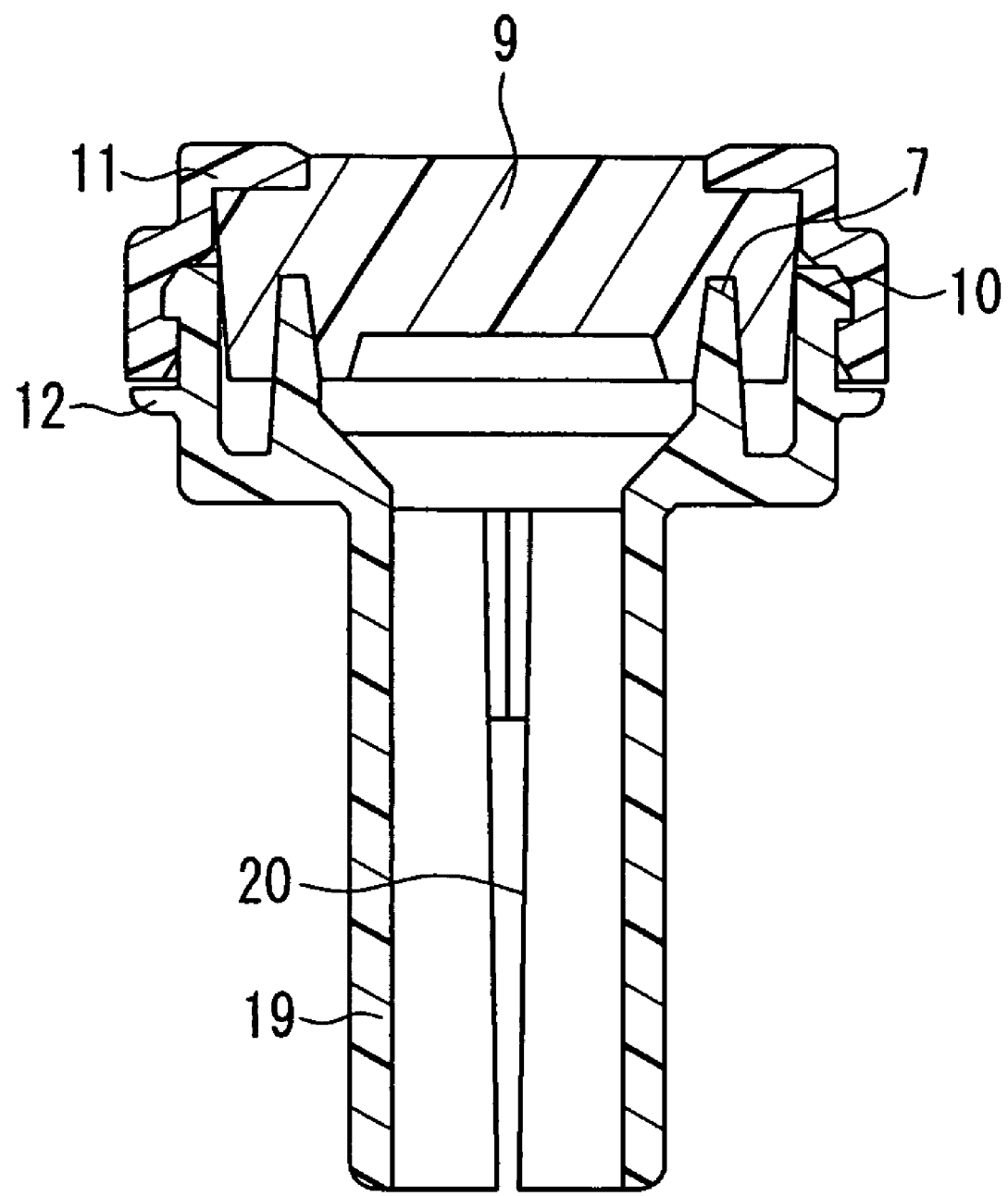
FIG. 7 is a cross-sectional view taken along the line B-B of the communicating member shown in FIG. 3.
Figure 8:
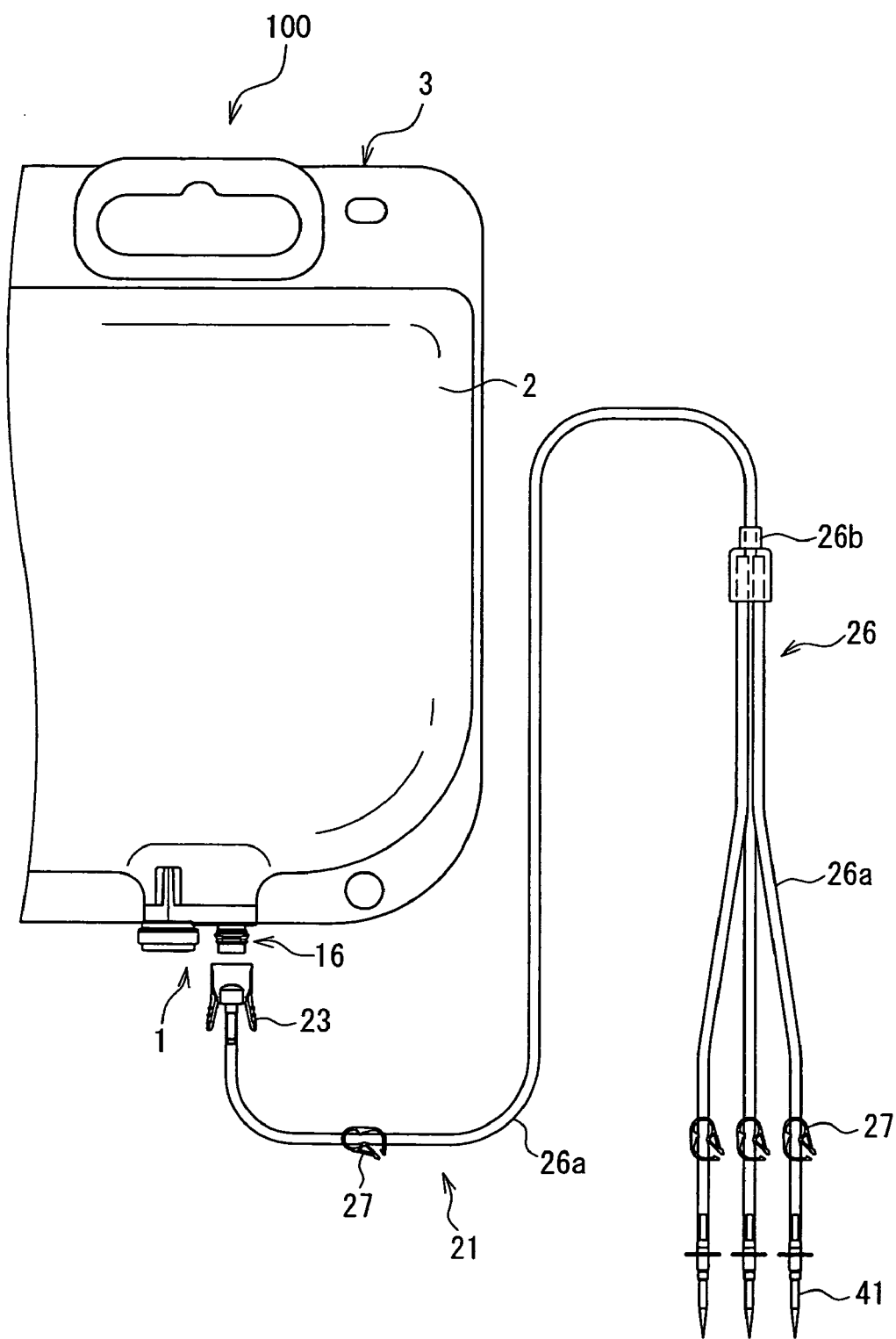
FIG. 8 is a plan view of an example of an infusion preparation tool set including a medical container in which the communicating member shown in FIG. 1 is used and a fluid-sending route that is to be connected to the medical container.

FIG. 1 is a perspective view of an example of the communicating member of the present invention, and FIG. 2 is a cross-sectional view taken along the line A-A of the communicating member shown in FIG. 1. FIG. 3 is a front view, FIG. 4 is a plan view, FIG. 5 is a bottom view, FIG. 6 is a side view, and FIG. 7 is a cross-sectional view taken along the line B-B of the communicating member of FIG. 3. FIG. 8 is a front view of an example of an infusion preparation tool set including the medical container in which the communicating member shown in FIG. 1 is used and a fluid-sending route that is to be connected to the medical container.

As shown in FIG. 8, an example of the communicating member 1 of the present invention is used while being fixed to a main container unit 3 composed of a flexible sheet 2, and constitutes a part of a medical container 100.

As shown in FIG. 2, a plate member 4 that constitutes the communicating member 1 includes a first opening 5 and a second opening 6. A first pedestal 7 and a second pedestal 8 are disposed generally perpendicularly on the plate member 4. The first pedestal 7 is in communication with the first opening 5, and the second pedestal 8 is in communication with the second opening 6. A plug 9 that obturates the opening on the tip side of the first pedestal 7 is provided in the tip portion of the first pedestal 7. The tip portion 7a of the first pedestal 7 is press-fit in an annular depressed portion 9a of the plug 9. Moreover, an annular engagement portion 10 is disposed upright on the plate member 4 such that the annular engagement portion 10 encloses the first pedestal 7, and the annular engagement portion 10 is provided with a hook 10a at its tip. This hook 10a and a hook 11a of a cap 11 into which the plug 9 is inserted are in engagement with each other, and thereby the plug 9 is sandwiched between the first pedestal 7 and the cap 11. The cap 11 covers only the edge of the surface 9b of the plug 9 (the surface opposite the surface facing the inner space of the first pedestal 7). Therefore, a metal needle or a synthetic resin needle (hereinafter referred to also as an "introducer needle") or the like that has a sharp tip can be inserted into the central part of the plug 9.

On the side opposite the first pedestal 7 side of the plate member 4, a first approximately cylindrical member 19 that is in communication with the first pedestal 7 and the first opening 5 are disposed generally perpendicularly on the plate member 4. As shown in FIG. 1, a part 19a of the peripheral surface of the first approximately cylindrical member 19 shares substantially the same plane as a part of the outer surface of a continuous wall 17. The approximately cylindrical member 19 has sufficient length so that the sheet 2 that constitutes the main container unit 3 (see FIG. 8) does not get broken by a metal needle or an introducer needle that penetrates the plug 9 when the metallic needle or the like is inserted into the plug 9.

As described above, in the communicating member 1 shown in FIG. 1 to FIG. 7, the first connection port 15 is composed of the first opening 5, the first pedestal 7 disposed upright to the first opening 5, the plug 9, the annular engagement part 10, the cap 11, and the first approximately cylindrical member 19.

A restrictor 12 disposed on the annular engagement portion 10 substantially in parallel with the plate member 4 is, for example, an annular rib and prevents an excessive movement of the cap 11 in the direction of the plate member 4 side.

Figure 9:
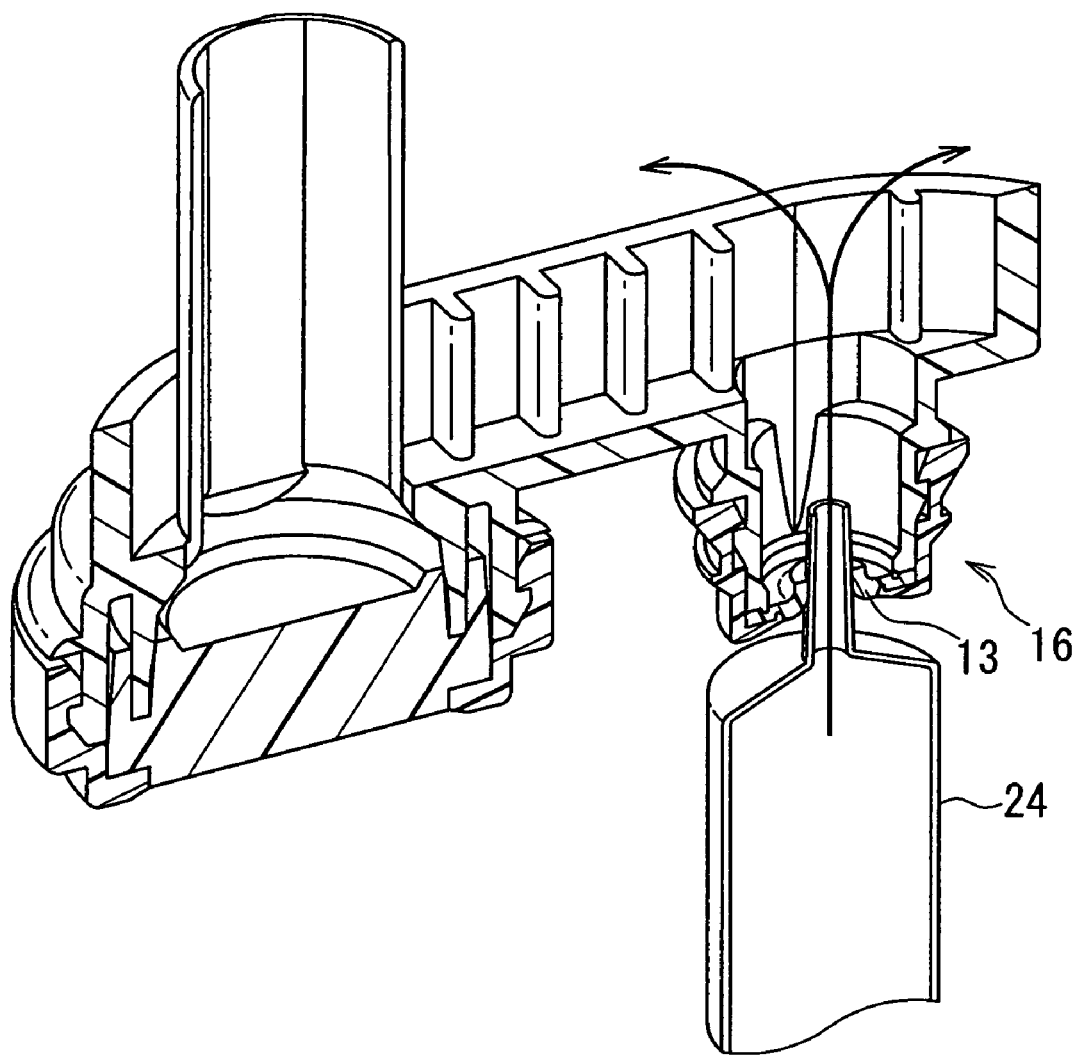
FIG. 9 is an explanatory perspective view showing a use of an example of the communicating member of the present invention.

As shown in FIG. 2, a barrier member 13 that obturates the opening located on the tip side of the second pedestal 8 is disposed in the tip portion of the second pedestal 8. The shape or other features of the barrier member 13 are not particularly limited. It is preferable that, for example, the barrier member 13 is a disc-like valve that has a linear slit 13a formed in the center. The end face 8a at the tip of the second pedestal 8 is in contact with the periphery of the back surface of the barrier member 13 (the surface facing the inner space of the second pedestal 8) and supports the barrier member 13. A latching projected portion 8b is provided on the peripheral surface of the second pedestal 8. The latching projected portion 8b is engaged with a latching depressed portion 14a provided on the covering member 14 that supports the barrier member 13, and thereby, the covering member 14 is held on to the second pedestal 8. The covering member 14 covers only the edge of the surface 13b of the barrier member 13 (surface opposite the surface facing the inner space of the second pedestal 8). Therefore, for example, the tip part (male luer) of a needleless syringe 24 can be inserted into the slit of the barrier member 13, and a small amount of medical fluid such as insulin can be injected for mixing, as shown in FIG. 9.

As described above, in the communicating member 1 shown in FIG. 1 to FIG. 7, the second connection port 16 is composed of the second opening 6, the second pedestal 8, the barrier member 13, and the covering member 14.

The continuous wall 17 is provided on the side opposite the first pedestal 7 side of the plate member 4, i.e., on the first approximately cylindrical member 19 side of the plate member 4. The continuous wall 17 is disposed substantially upright on the plate member 4 such that the continuous wall 17 encloses the first opening 5 and the second opening 6 when the plate member 4 is viewed from above. In this embodiment, as shown in FIG. 1 and FIG. 2, the width of the plate member 4 is tapered gradually toward both ends when viewed from above, and there is a convergence point at both ends. That is, the plate member 4 has a planar shape similar to the bottom plate of a boat. Therefore, when the communicating member 1 is secured to the sheet 2 by heat sealing after sandwiching the continuous wall 17 portion of the communicating member 1 with two pieces of the sheet 2 (see FIG. 8) that constitutes the main container unit 3, the phenomenon of a sealing failure at the boundary of where the two pieces of the sheet 2 are adhered to each other and where the sheet 2 and the continuous wall 17 are adhered can be prevented, and thus such a configuration is preferable. Moreover, if a plurality of reinforcing ribs 18 are provided integrally with the plate member 4 on the inner surface of the continuous wall 17, deformation of the communicating member 1 is suppressed when carrying out heat sealing, and thus such a configuration is preferable.

The first approximately cylindrical member 19 that constitutes the first connection port 15 is provided with a first communicating portion 20 that has an opening on the second opening 6 side. As shown in FIG. 7, the first communicating portion 20 may be formed by providing a slit in the cylindrical wall of the first approximately cylindrical member 19 in the longitudinal direction over the entire length. Therefore, even when air bubbles enter the inner space of the first connection port 15, the air bubbles can be moved outside the first connection port 15 toward the second opening 6 side through the slit. The air bubbles arrived at the second opening 6 side through the slit are moved toward the surface side of the fluid stored in the main container unit 3 due to, for example, buoyancy. In addition, for example, when the fluid-sending route 21 and the main container unit 3 as shown in FIG. 8 are in communication, the air bubbles can be discharged into the fluid-sending route 21.

Thus, with the communicating member 1 having the above-described configuration, it is easy to move air bubbles that have entered into the inner space of the first connection port 15 to near the second opening that is outside the first connection port 15. Therefore, the retention of air in the inner space of the first connection port 15 can be suppressed. Hence, with the medical container in which the communicating member 1 of this embodiment is used, it is easy to perform gas-liquid separation in the medical container.

As shown in FIG. 3, if the first approximately cylindrical member 19 is sectioned into a part 19b that is relatively closer to the second opening and a part 19c that is relatively farther, the position where the first communicating portion 20 (see FIG. 1) is provided is not limited in as long as the first communicating portion 20 has an opening in the part 19b that is relatively closer to the second opening 6 (see FIG. 2). It is, however, preferable that, the first communicating portion 20 is provided in a position where the first communicating portion 20 is not blocked by the sheet 2 that constitutes the main container unit 3 of the medical container 100 when the medical container 100 is vibrated or when the medical container 100 is overturned to remove air bubbles entered into the inner space of the first connection port 15. Specifically, it is preferable that an opening is formed in a position within the part 19b that is closer to the second opening on the peripheral surface of the first approximately cylindrical members 19 but not in the part 19a that is on the same plane as the continuous wall 17. In particular, as shown in FIG. 5, it is preferable that, when the communicating member 1 is viewed from above so that the inner space of the first approximately cylindrical member 19 can be seen, the first communicating portion 20 is formed such that the first communicating portion 20 overlaps a part of the line connecting the center of the plug 9 and the center of the barrier member 13. In this case particularly, it is easy to remove air bubbles from the inside of the first connection port 15 and it is unlikely that the sheet that constitutes the main container unit gets broken by a metal needle, plastic needle or the like that has a sharp tip.

Figure 10:
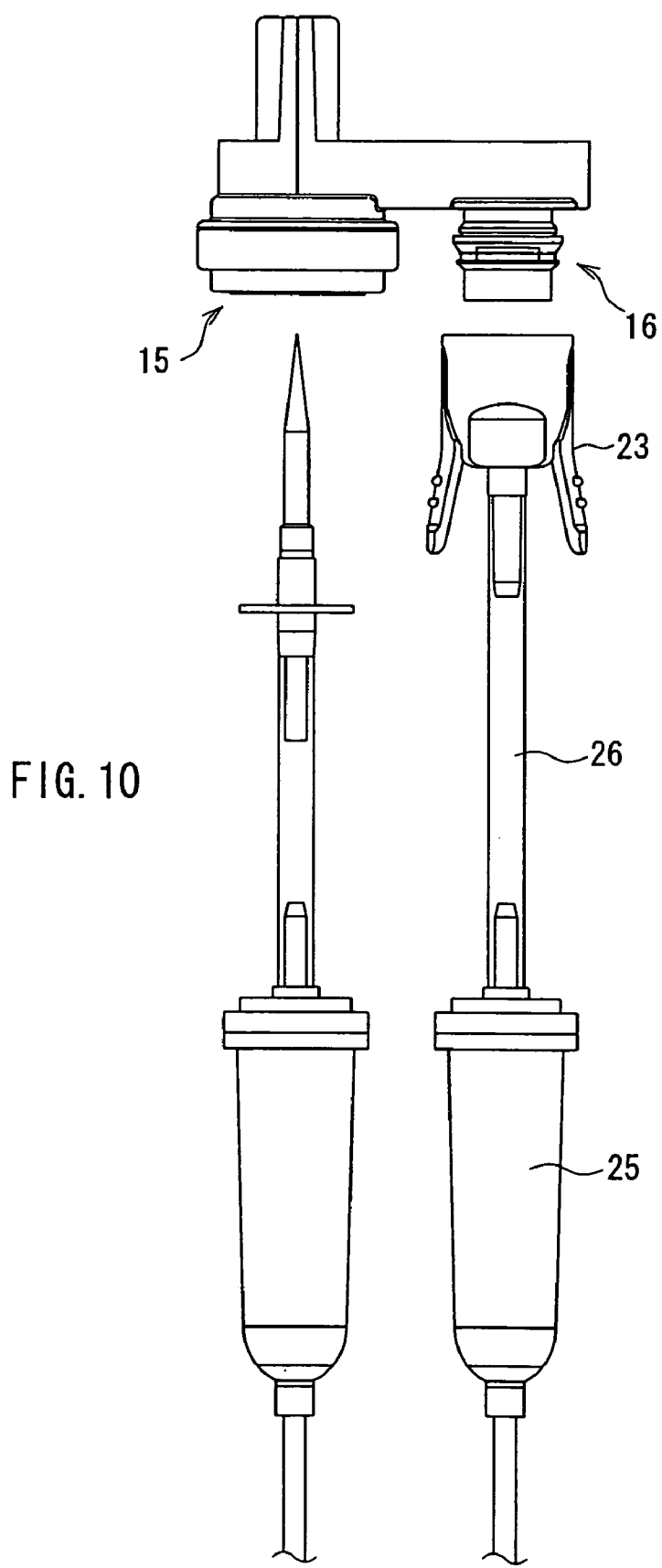
FIG. 10 is an explanatory front view showing a use of an example of the communicating member of the present invention.

In addition to the fluid-sending route 21 shown in FIG. 8 and the needle-less syringe 24 shown in FIG. 9, an infusion set provided with the same lock connector 23 as the lock connector 23 that constitutes the fluid-sending route 21 shown in FIG. 8 can be connected to the second connection port 16 as shown in FIG. 10. The configuration of the infusion set may be identical to that of a conventional infusion set except for being provided with the lock connector 23. Specifically, for example, the lock connector 23, an infusion cylinder 25 and a needle (not shown) inserted into the vein are connected via a flexible tube 26. Moreover, the infusion set may be provided, as necessary, with a flow control means (not shown) between the infusion cylinder 25 and the needle for controlling the flow rate of the fluid that flows inside the infusion set. FIG. 8 shows an example of the fluid-sending route 21. It is sufficient that the fluid-sending route that constitutes the infusion preparation tool set of this embodiment includes the fluid sending tube 26, a connecting means that is disposed at one end of the fluid-sending tube 26, that allows a communicating path that brings the inside of the main container unit 3 of the medical container 100 and the fluid-sending tube 26 into communication to be formed, and that can maintain the state of the communicating path being formed, and a needle 41 disposed at the other end of the fluid-sending tube.

The second connection port 16 functions as a port where fluid flows in when the fluid-sending route 21 is connected as shown in FIG. 8. As shown in FIG. 9, when the needle-less syringe 24 in which medical fluid for mixed injection is filled is connected, the second connection port 16 functions as a port for mixed injection. As shown in FIG. 10, when an infusion set is connected, the second connection port 16 functions as a fluid discharge port.

The first connection port 15 functions as a fluid discharge port when the introducer needle of a conventional infusion set is inserted into the plug 9 (see FIG. 2) as shown in FIG. 10, and functions as a mixed injection port when the injection needle (not shown) of a syringe filled with medical fluid for mixed injection is inserted.

The first approximately cylindrical member 19 further may be provided with a second communicating portion 22 that has an opening on the side opposite the second opening side as shown in FIG. 5. Air bubbles may stay on the side opposite the second opening side around the first approximately cylindrical member 19. In this case, by giving a vibration to the medical container or performing a similar action, air bubbles can be moved from the second communicating portion 22 to the inner space of the first approximately cylindrical member 19. The air bubbles that entered into the inner space of the first approximately cylindrical member 19 can be moved from the first communicating portion 20 toward the second opening 6 side that is outside the first approximately cylindrical member 19. It is preferable that the second communicating portion 22 is located opposite the first communicating portion 20.

In the communicating member 1 described above with reference to drawings, the first communicating portion 20 and the second communicating portion 22 both are formed by providing slits in the cylindrical wall of the first approximately cylindrical member 19 in the longitudinal direction over the entire length. However, the form of the first communicating portion 20 and the second communicating portion 22 is not limited thereto. For example, the slits may be provided from the middle section up to the tip of the first approximately cylindrical member 19 in the longitudinal direction. In addition, the first communicating portion 20 may be formed by providing a through-hole that penetrates the cylindrical wall of the first approximately cylindrical member 19 in the thickness direction. In particular, it is easy to remove air bubbles entered into the inner space of the first pedestal 7 when the first communicating portion 20 is formed near the plug 9, and such a configuration is preferable. It is therefore preferable that the first communicating portion 20 is provided at least in the base portion of the first approximately cylindrical member 19.

The material of the plate member 4 is not particularly limited, and rigid materials are preferable, for example, rigid plastic including resins such as polypropylene, polyethylene, polycarbonate, polyvinyl chloride and the like.

The materials of the continuous wall 17, the first approximately cylindrical member 19, the first pedestal 7, the second pedestal 8, the annular engagement portion 10 and the reinforcing ribs 18 are preferably identical to that of the plate member 4, and it is preferable that these components and the plate member 4 are formed integrally using the same material, in particular, according to the injection molding method.

The material of the plug 9 is not particularly limited, and any material known to be for use in a plug that constitutes a connection port of a conventional medical container can be used. Examples include materials that have rubber-like elasticity, such as silicone rubber, isoprene rubber, butyl rubber, etc.

The material of the cap 11 is not particularly limited, and examples include resins such as polypropylene, polyethylene, polycarbonate, polyacetal, polyamide, polyvinyl chloride, etc.

The material of the barrier member 13 is not particularly limited, and commonly used materials that show rubber-like elasticity are sufficient. For example, those that have a JIS-A hardness of 20 to 60 are preferable. Specific examples of materials are synthetic rubbers such as silicone rubber, isoprene rubber, butyl rubber, nitrile rubber and the like, thermoplastic elastomers, etc.

The material of the covering member 14 is not particularly limited, and examples include polypropylene, polyethylene, polycarbonate, polyacetal, polyamide, polyvinyl chloride, etc.

The material of the flexible sheet 2 that constitutes the medical container 100 is not particularly limited, and examples include vinyl chloride resin, polyethylene, ethylene-vinyl acetate copolymer, polyester, polybutadiene, polypropylene, polyamide, ethylene-methacrylate copolymer, etc. The thickness of the sheet 2 is also not limited, and the thickness of, for example, about 0.1 to 0.4 mm is suitable.

The shape of the main container unit 3 is also not particularly limited, and the main container unit 3 may be, for example, rectangular, elliptical, etc. It is preferable that the lower part of the main container unit 3 is inclined slightly toward the fluid discharge port so that the medical fluid or the like in the medical container 100 can flow easily into the fluid discharge port.

(Embodiment 2)

Embodiment 2 is an example of an infusion preparation tool set that includes the medical container described in Embodiment 1 and a fluid-sending route that is to be connected to the medical container.

The infusion preparation tool set is composed of the medical container 100 and the fluid-sending route 21 as shown in FIG. 8. This infusion preparation tool set is used, for example, when supplying to a patient a nutrient preparation (high-calorie infusion fluid) containing amino acid, sugar, lipid, vitamin, etc. Each ingredient, such as amino acid, is stored separately in, for example, a vial, and high-calorie infusion fluid is prepared immediately before administration into a patient by mixing the ingredients in the medical container 100.

In the fluid-sending route 21, the fluid-sending tube 26 branches off in the middle section and is composed of flexible tubes 26a and a branch connection tube 26b that unites the flexible tubes 26a. Needles 41 (for example, synthetic resin needles or metal needles) that are inserted into the mouth of vials or the like and enable the inside of the vials and the fluid-sending tube 26 to be in communication are disposed at one end of the fluid-sending tube 26. A lock connector 23 is disposed at the other end of the fluid-sending tube 26. The flexible tubes 26a are furnished with clamps 27 that can open or block the passage in the flexible tubes 26a.

Next, the lock connector 23 shall be described in detail with reference to FIG. 11 to FIG. 14.

Figure 11:
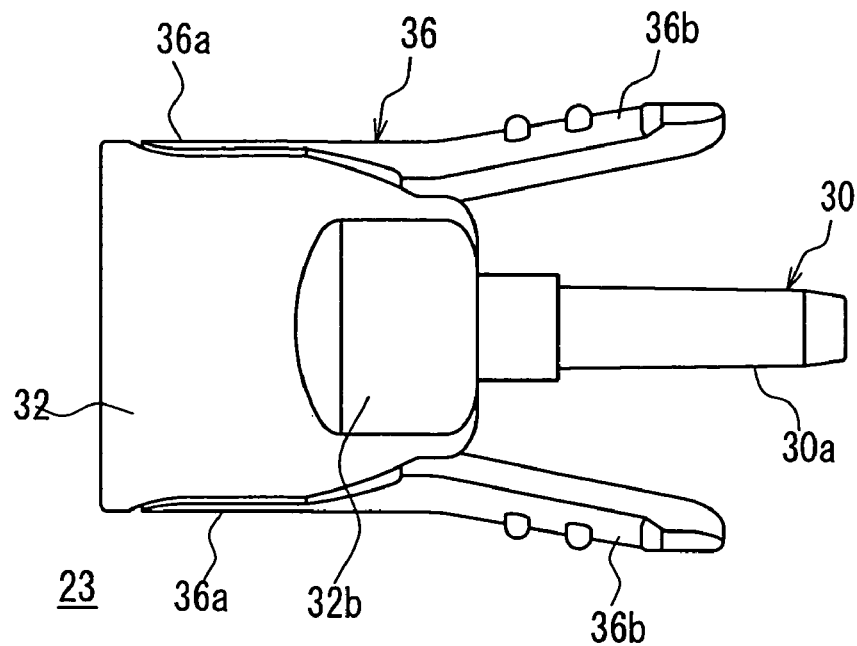
FIG. 11 is a side view showing the lock connector of the fluid-sending route that constitutes an example of the infusion preparation tool set of the present invention.

The lock connector 23 has a conduit portion 30 in the center as shown in the side view presented in FIG. 11. Although only the base portion 30a of the conduit portion 30 is shown in FIG. 11, the conduit portion 30 includes a tip portion 30b as can be understood from the cross-sectional view of FIG. 12. To the base portion 30a is connected the fluid-sending tube 26 (see FIG. 8). The tip portion 30b penetrates the barrier member 13 of the second connection port 16 of the medical container 100 and reaches the inner space of the second connection port 16.

Figure 12:
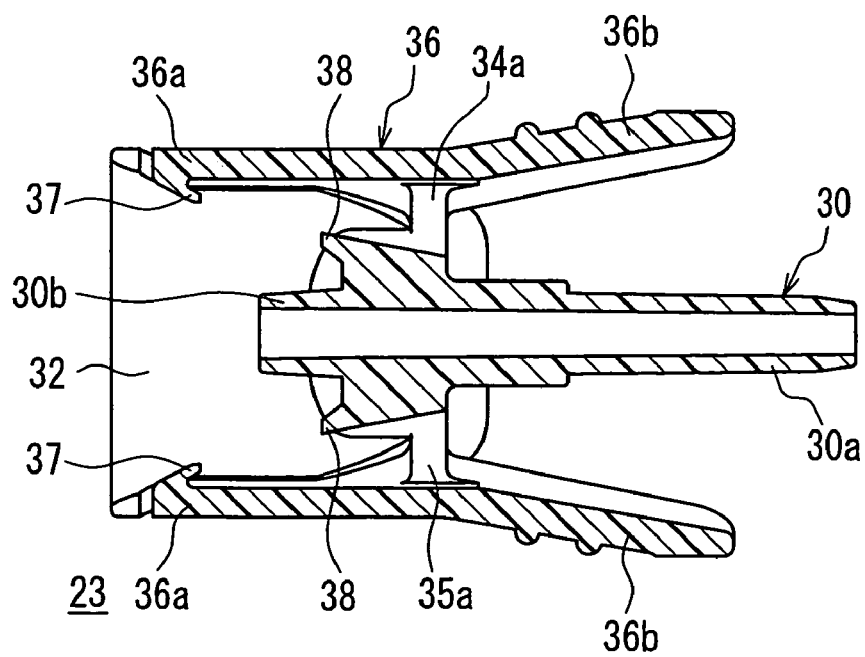
FIG. 12 is a cross-sectional view of the lock connector shown in FIG. 11.
Figure 13:
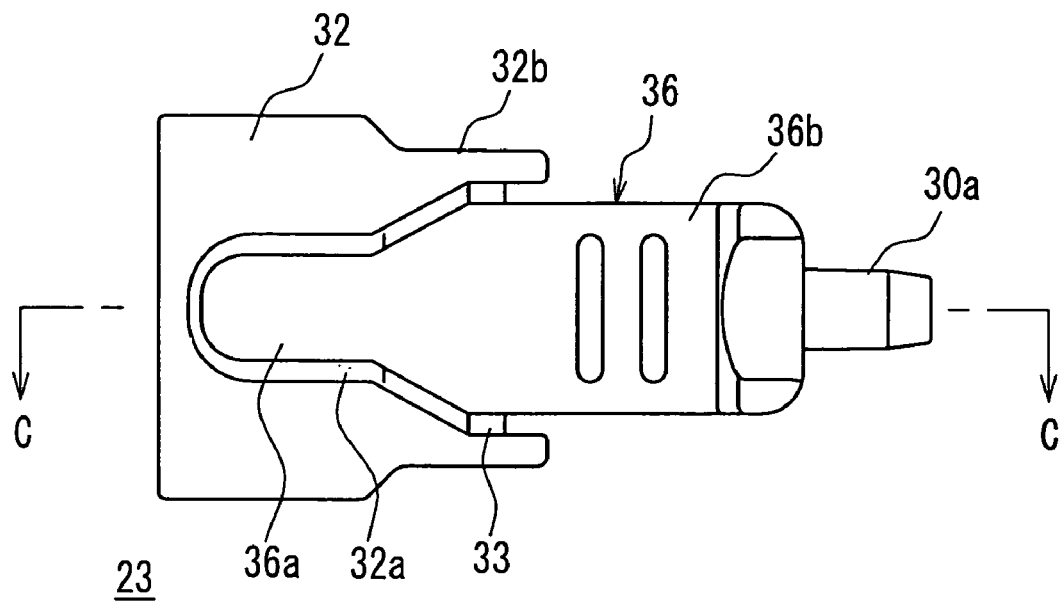
FIG. 13 is another side view of the lock connector shown in FIG. 11.

An approximately cylindrical hood 32 is disposed such that the tip portion 30b of the conduit portion 30 is enclosed as shown in FIG. 11 and FIG. 12. The hood 32 on the base side is joined with the axial middle section of the conduit portion 30. The joined portion 33 of the hood 32 and the conduit portion 30 are shown in another side view presented in FIG. 13 or a front view presented in FIG. 14. The hood 32 has a notch 32a on its cylindrical continuous wall as shown in FIG. 13. FIG. 12 shows a cross section taken along the line C-C given in FIG. 13.

Figure 14:
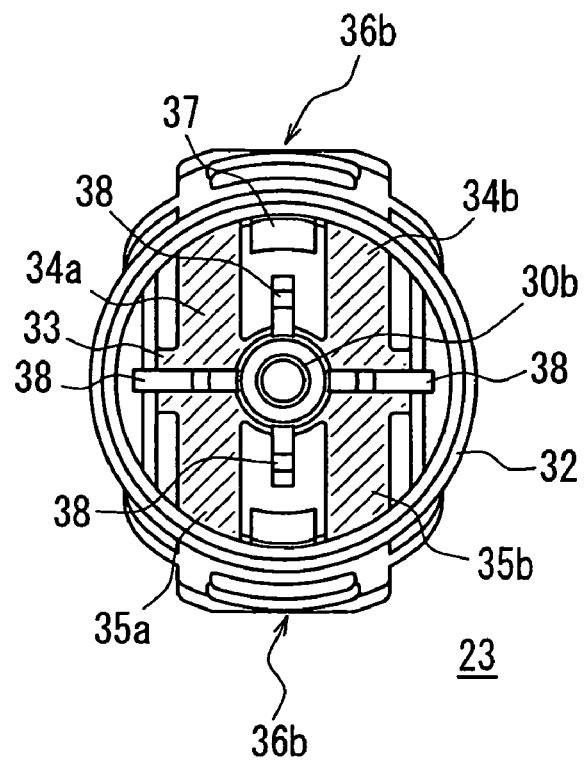
FIG. 14 is a front view of the lock connector shown in FIG. 11.

In addition to the hood 32, supports 34a, 34b, 35a and 35b are joined with the middle section of the conduit portion 30 and each of these supports extends in the direction perpendicular to the axis of the conduit portion 30 as shown in FIG. 12 and FIG. 14. For viewability, hatching is given to the supports 34a, 34b, 35a and 35b in FIG. 14. In FIG. 11 and FIG. 12, the reference numeral 36 refers to a locking lever. A pair of locking levers 36 are disposed on the lateral part of the conduit portion 30, and each locking lever extends in the axial direction of the conduit portion 30. The middle section of the locking levers 36 is joined with the tip of the supports 34a, 34b, 35a and 35b, thereby being positioned at specific locations relative to the conduit portion 30. The supports 34a and 34b as a pair support one locking lever 36, and the supports 35a and 35b as a pair support the other locking lever 36. Therefore, in a practical sense, a pair of supports are provided per locking lever 36.

The locking levers 36 are provided with locking pieces 36a on the tip side thereof when viewed from the joined portions formed with the supports 34a, 34b, 35a and 35b and are provided with operation pieces 36b on the base side thereof. Each locking piece 36a has at its tip a locking claw 37 that projects inward. Each locking piece 36a is placed within the notch 32a of the hood 32, and as shown in FIG. 13 and FIG. 14, the outer surface of the locking levers is arranged to be substantially on the same plane as the outer surface of the hood 32. Since the notch 32a is closed on the tip side, the tip of the locking pieces 6a of the locking levers 6 is enclosed by the hood 32 when viewed from above, thereby reducing the possibility of coming into contact with other objects when used.

By applying a pressure in the direction of the conduit portion 30 to the operation pieces 36b of the locking levers 36, i.e., by applying a force as if pinching the operation pieces 36b of the pair of locking levers 36 shown in FIG. 11 or FIG. 12, the supports 34a, 34b, 35a and 35b are deformed resiliently. Thereby, the locking levers 36 are moved around near the joined portions formed with the supports 34a, 34b, 35a and 35b, and the space between the pair of locking claws 37 becomes larger.

Positioning parts 38 are provided near the joined portion of the conduit portion 30 and the hood 32 as shown in FIG. 12 and FIG. 14. The positioning parts 38 are placed around the conduit portion 30 within the hood 32 in the shape of a cross, and has a function to position the conduit portion by being contacted with the tip of the second connection port 16 (see FIG. 2) when the second connection port 16 to be connected enters the hood 32. Thereby, the conduit portion 30 is prevented from being wobbly once inserted into the second connection port 16, and a stable connected state can be obtained.

Moreover, grippers 32b that are formed by partially flattening the cylindrical surface are provided on the base side of the hood 32 as shown in FIG. 11 and FIG. 13. These grippers 32b are provided for enhancing the ease of operation such that when the connector is connected, these grippers are held.

It is preferable that the components described above are configured as a single unit. The materials thereof are required to have a hardness sufficient to have the conduit portion 30 penetrate the barrier member 13 (see FIG. 2) and an elasticity (flexibility) sufficient for attachment/detachment operations. For example, polycarbonate, polypropylene and the like are preferable.

Next, the configuration of the second connection port 16 to which the above-described lock connector 23 is connected shall be described with reference to FIG. 2 and FIG. 3.

As described in Embodiment 1, the tip portion 30b of the conduit portion 30 of the lock connector 23 can be inserted into the inner space of the second pedestal 8. The covering member 14 is provided at the tip of the second pedestal 8 with the barrier member 13 being interposed. The barrier member 13 obturates the tip portion of the second pedestal 8, and is held by the tip of the second pedestal 8 and the inner surface of the distal projected portion 14b of the covering member 14. In order to ensure that the barrier member 13 is held securely, a projection 8b is formed at the tip of the second pedestal 8, a projection 14c is also formed on the inner surface of the distal projected portion 14b of the covering member 14, and the barrier member 13 is sandwiched by the projection 8b and the projection 14c.

As shown in FIG. 3, two annular projected portions are disposed on the peripheral surface of the covering member 14, and thereby, the second connection port has the first protrusion 14d and the second protrusion 14e. The locking claws 37 formed on the locking pieces 36a of the lock connector 23 can be engaged with the first and second protrusions 14d and 14e (see FIG. 12 and other drawings). When the locking claws 37 are in the state of engagement with the first protrusion 14d, the lock connector 23 and the second connection port 16 are connected shallowly, and the state in which the tip portion 30b of the conduit portion 30 of the lock connector 23 does not penetrate the barrier member 13 is maintained. When the locking claws 37 are in the state of engagement with the second protrusion 14e, the lock connector 23 and the second connection port 16 are connected deeply, and the state in which the tip portion 30b of the conduit portion 30 of the lock connector 23 penetrates the barrier member 13 is maintained.

Figure 15A:
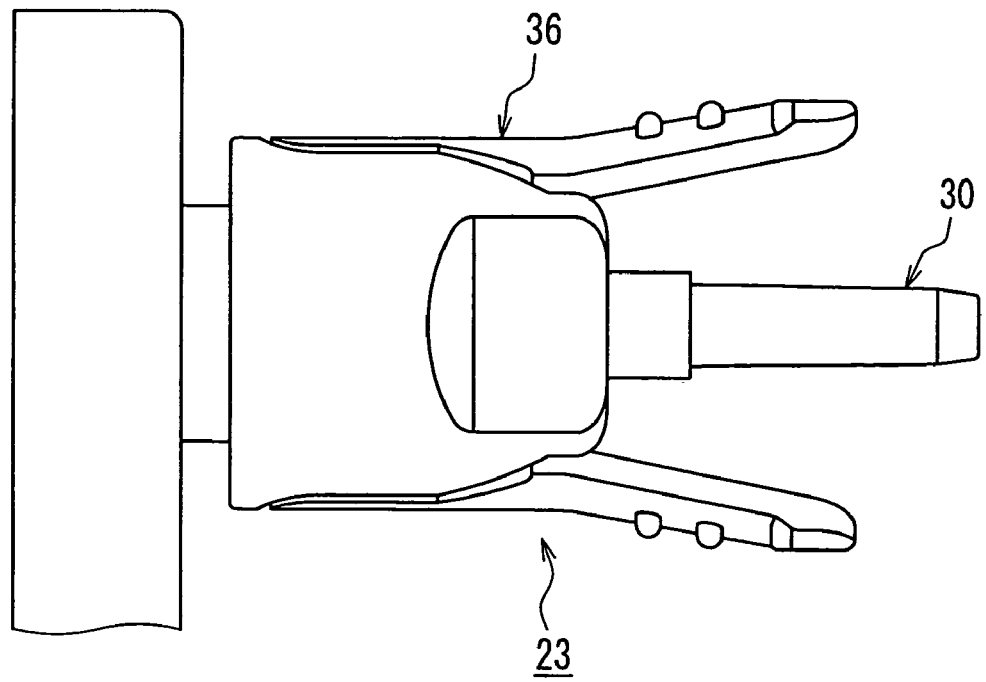
FIG. 15A is an explanatory side view showing a first connected state of the second connection port and the lock connector shown in FIG. 11 that constitute an example of the infusion preparation tool set of the present invention.
Figure 15B:
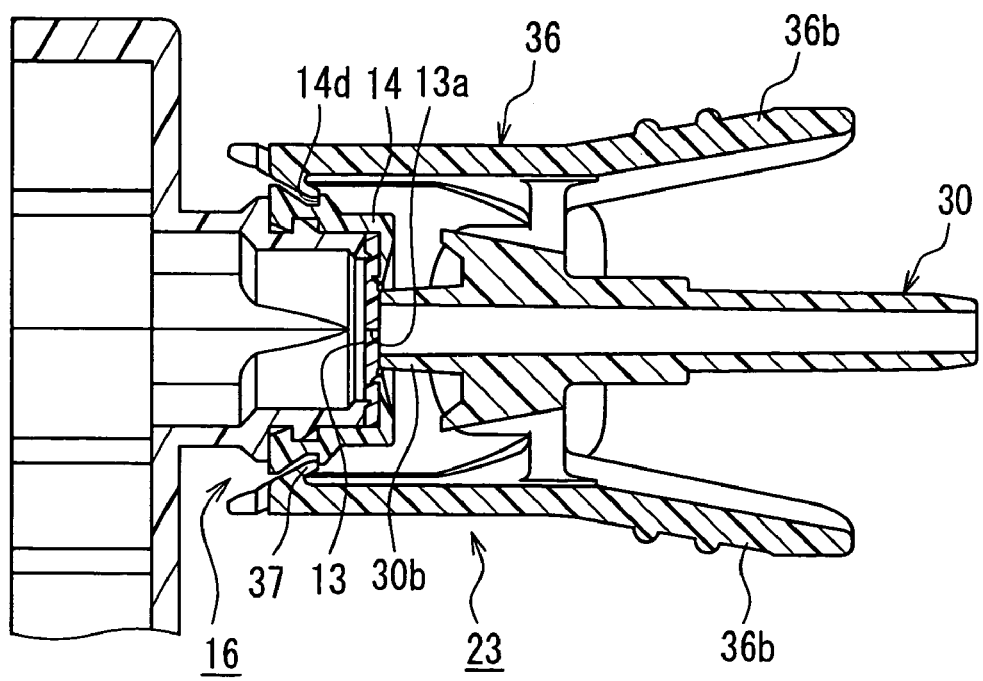
FIG. 15B is a cross-sectional view of the components shown in FIG. 15A.

Next, a connection operation for the second connection port 16 and the lock connector 23 shall be described. When the lock connector 23 and the second connection port 16 are connected, the tip of each component is faced with each other, and the covering member 14 of the second connection port 16 is inserted into the hood 32 of the lock connector 23. Thereby, the tip portion 30b of the conduit portion 30 of the lock connector 23 contacts the barrier member 13. As shown in FIG. 15A and FIG. 15B, the locking claws 37 of the lock connector 23 then are engaged with the first protrusion 14d of the covering member 14. In this first connected state, the connection of the lock connector 23 and the second connection port 16 is maintained while the tip portion 30b of the conduit portion 30 of the lock connector 23 do not penetrate the barrier member 13 of the second connection port 16. Therefore, the passage of the lock connector 23 and the passage of the second connection port 16 are not in communication.

Figure 16A:
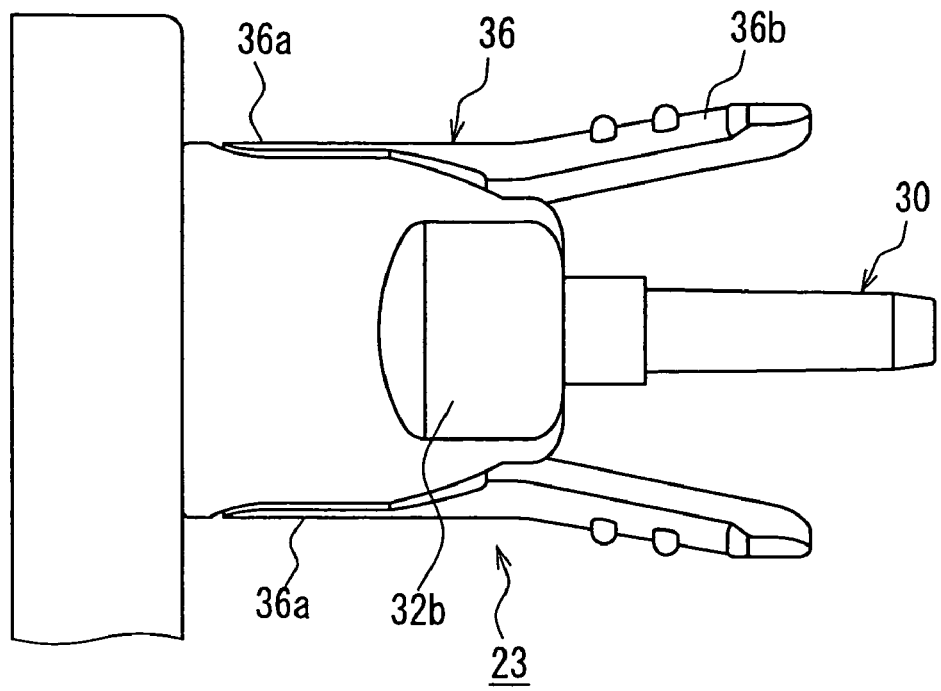
FIG. 16A is an explanatory side view showing a second connected state of the second connection port and the lock connector shown in FIG. 11 that constitute an example of the infusion preparation tool set of the present invention.
Figure 16B:
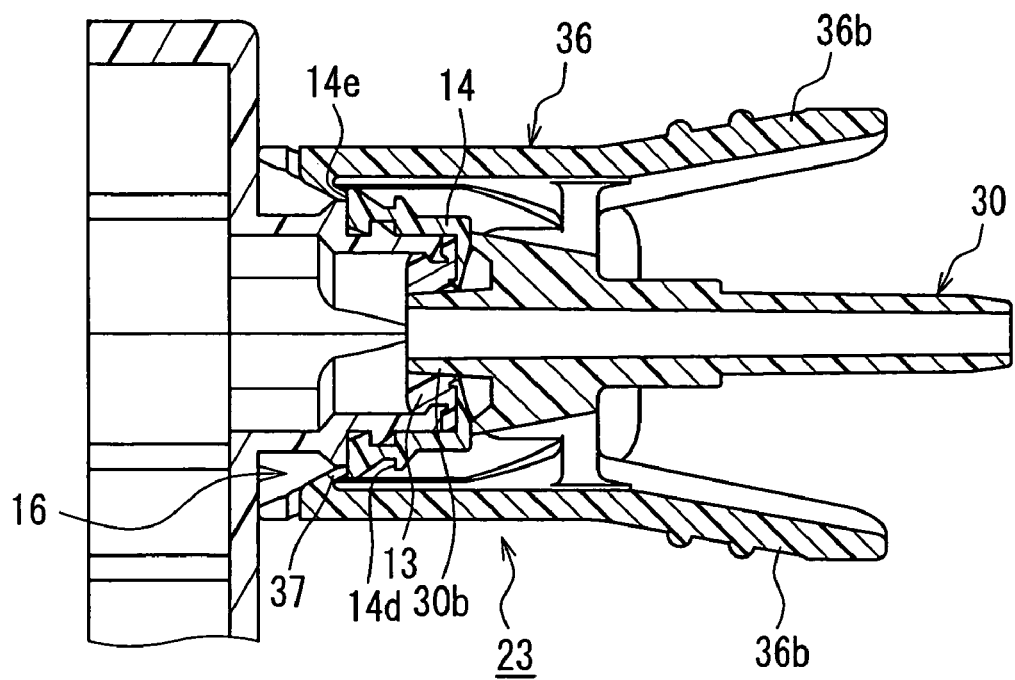
FIG. 16B is a cross-sectional view of the components shown in FIG. 16A.

From this state, the connection of the lock connector 23 and the second connection port 16 is deepened as shown in FIG. 16A and FIG. 16B, and thus it is possible to engage the locking claws 37 of the locking levers 36 and the second protrusion 14e. In this second connected state, the connection of the lock connector 23 and the second connection port 16 is maintained while the tip portion 30b of the conduit portion 30 of the lock connector 23 penetrates the barrier member 13 of the second connection port 16. Therefore, the state in which the passage of the lock connector 23 and the passage of the second connection port 16 are in communication can be obtained.

To disconnect the lock connector 23 and the second connection port 16, a pressure in the direction of the conduit portion 30 is applied to the operation pieces 36b of the lock connector 23. Thereby, supports 34a, 34b, 35a and 35b (see FIG. 14) are deformed resiliently, and the distance between the pair of locking claws 37 is widened. As a result, the locking claws 37 and the first protrusion 14d or the second protrusion 14e are disengaged.

According to the above-described configuration and operation, the lock connector 23 is connected to the second connection port 16 in the first connected state shown in FIG. 15A and FIG. 15B, but the barrier member 13 of the second connection port 16 is not penetrated by the tip portion 30b of the conduit portion 30 of the lock connector 23, and therefore the generation of permanent deformation of the barrier member is avoided even when the infusion preparation tool set is stored for a long period of time.

The infusion preparation tool set may be configured such that the tip portion 30b of the conduit portion 30 of the lock connector 23 contacts the barrier member 13 of the second connection port 16 in the first connected state, and the pressure created thereby partially opens the slit 13a. Thus, it is possible to introduce sterilizing gas in the first connected state.

Figure 17A:
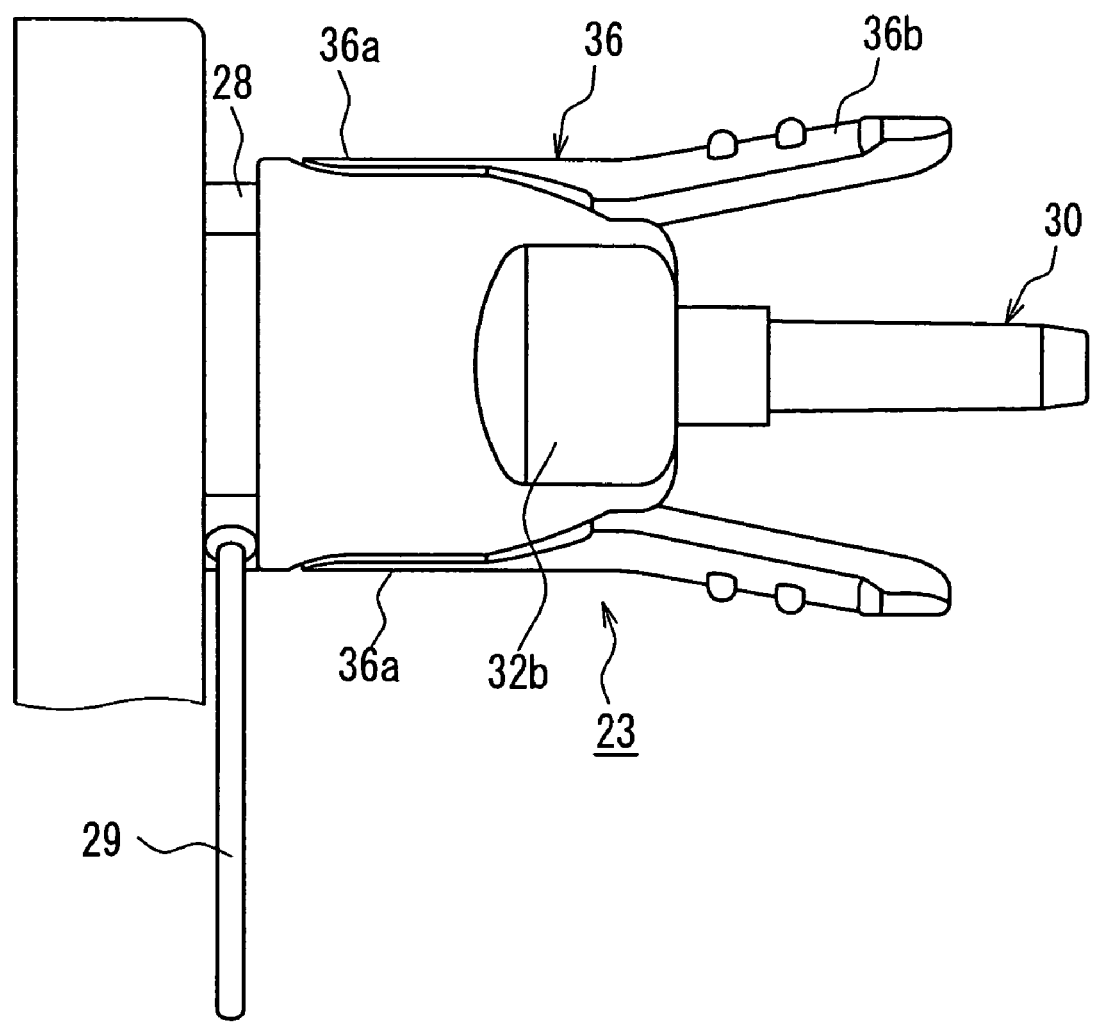
FIG. 17A is an explanatory side view showing a first connected state of the second connection port and the lock connector shown in FIG. 11 that constitute an example of the infusion preparation tool set of the present invention.
Figure 17B:
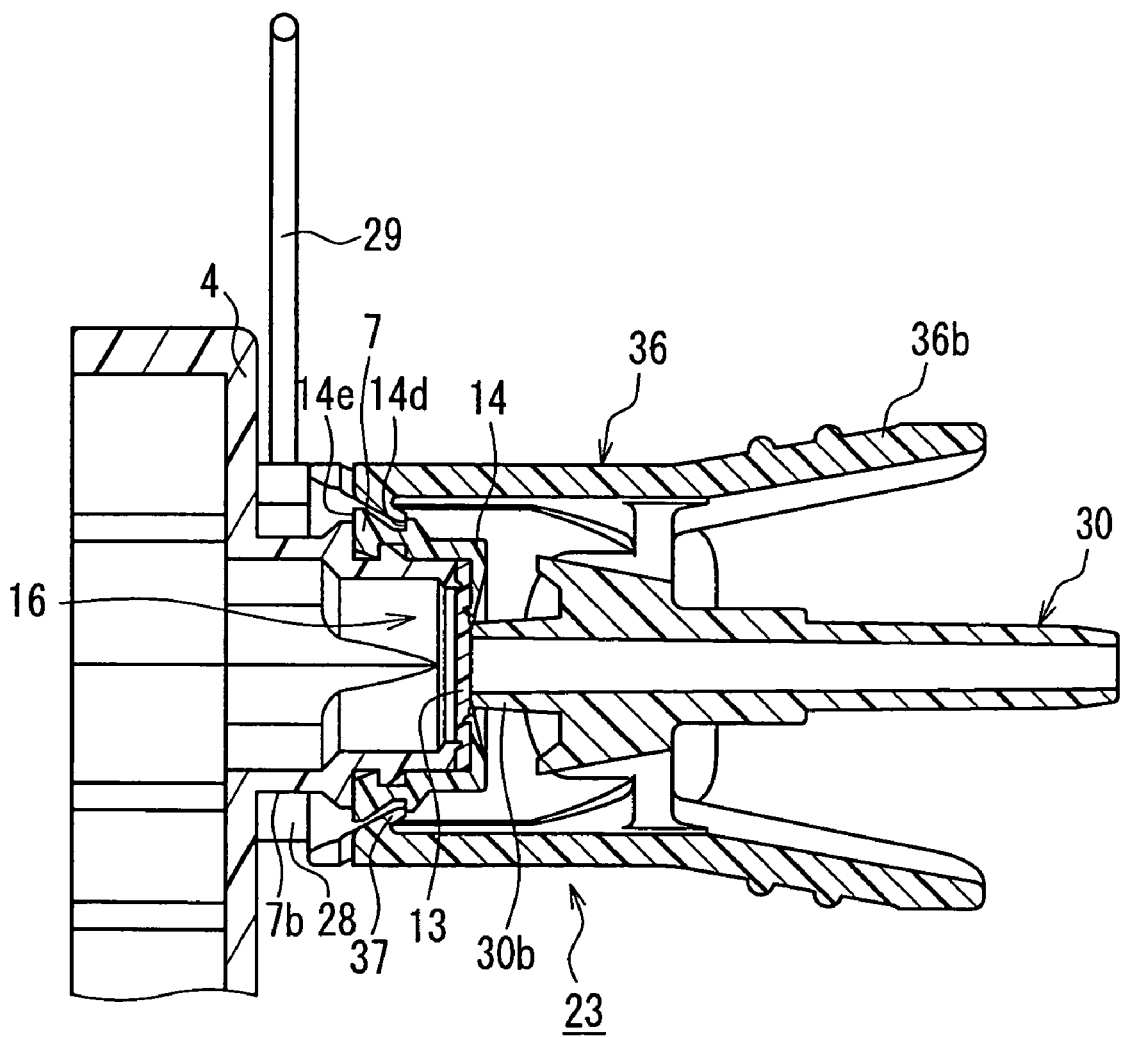
FIG. 17B is a cross-sectional view of the components shown in FIG. 17A.
Figure 18:
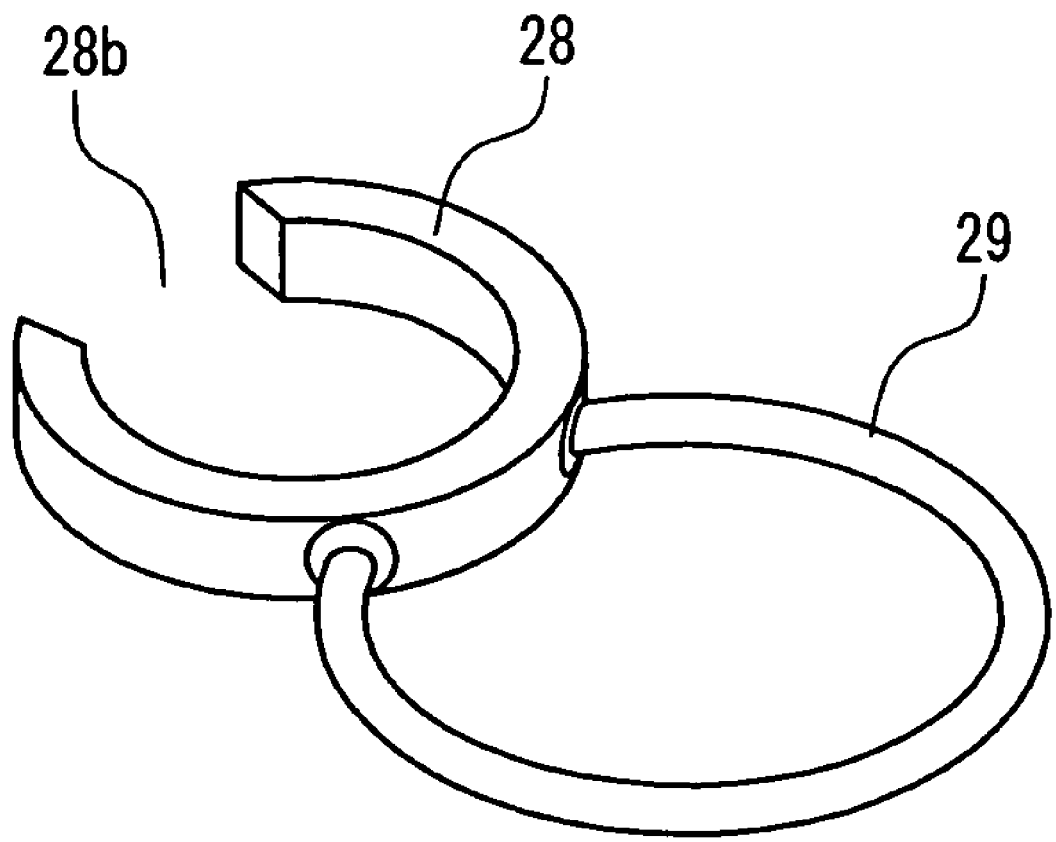
FIG. 18 is a perspective view showing a position regulator that constitutes an example of the infusion preparation tool set of the present invention.

A position regulating configuration is shown in FIG. 17A and FIG. 17B. This configuration is to prevent the engagement of the locking claws 37 of the lock connector 23 and the first protrusion 14d of the second connection port 16 from being deepened in order to maintain the first connected state shown in FIG. 15A and FIG. 15B securely. The second connection port 16 includes a reduced diameter portion 7b on the side closer to the base than the second protrusion and on the first pedestal side of the plate member 4. When the locking claws 37 of the locking levers 36 and the first protrusion 14d are in engagement, a c-shaped stopper 28 is installed on the reduced diameter portion 7b as a position regulator that prevents the second connected state. The c-shaped stopper 28 installed between the tip of the hood and the plate member 4 has a shape as shown in, for example, FIG. 18. The c-shaped stopper 28 has a shape of a ring with a gap 28b and is installed on the second connection port 16 through the gap 28b. A ring pull 29 is attached to the c-shaped stopper 28 for the ease of handling. The lock connector 23 is position-regulated with the c-shaped stopper 28, and thereby the connection of the second connection port 16 and the lock connector 23 is secured firmly while the barrier member 13 of the second connection port 16 is not penetrated by the tip portion 30b of the conduit portion 30 of the lock connector 23. Moreover, in this state, both the passage of the lock connector 23 and the passage of the second connection port 16 are positioned for communication as shown in FIG. 15A and FIG. 15B, and thus the operation of bringing these passages into communication is very easy.

As described above, it is possible to supply the infusion preparation tool set while the lock connector 23 and the second connection port 16 in the first connected state, and thus it is possible to eliminate the operation of connecting these components when used, and it is possible to prevent the contamination of the inside of the connector that may be caused by the outside contact with the connection parts. Furthermore, when the infusion preparation tool set is used, the lock connector 23 merely is pressed against the second connection port 16, and thus the operation is very simple. To disconnect, the operation pieces 36b merely are held with the fingers. In addition, the locking levers 36 are independent of the hood 32 and supported by the conduit portion 30 via the supports 34a, 34b, 35a and 35b (see FIG. 14). Therefore, a wide margin can be easily provided to resiliently change the position of the locking claws 37 that are provided at the tip of the locking pieces 36a. As a result, a sufficient margin can be secured for the engagement with the first and second protrusion 14d and 14e, and thus a secure engagement can be obtained.

Moreover, since the locking pieces 36a are enclosed completely by the hood 32 and since the outer surface thereof is substantially on the same plane as the outer surface of the hood 32, there is little possibility of the tip of the locking pieces 36a being deformed by an accidental contact with other object, thereby reducing the chances of accidental disengagement. Furthermore, due to the configuration that the tip portion 30b of the conduit portion 30 is housed in the hood 32, the tip portion 30b can be protected from contamination caused by a contact with other object, and thus it is possible to keep the portion that comes into contact with infusion fluid clean.

The infusion preparation tool set of this embodiment may be delivered to the market while the medical container 100 and the fluid-sending route 21 are in the first connected state, or the infusion preparation tool set may be delivered to the market while the medical container 100 and the fluid-sending route 21 are not in the state of connection as shown in FIG. 8.

Figure 19:
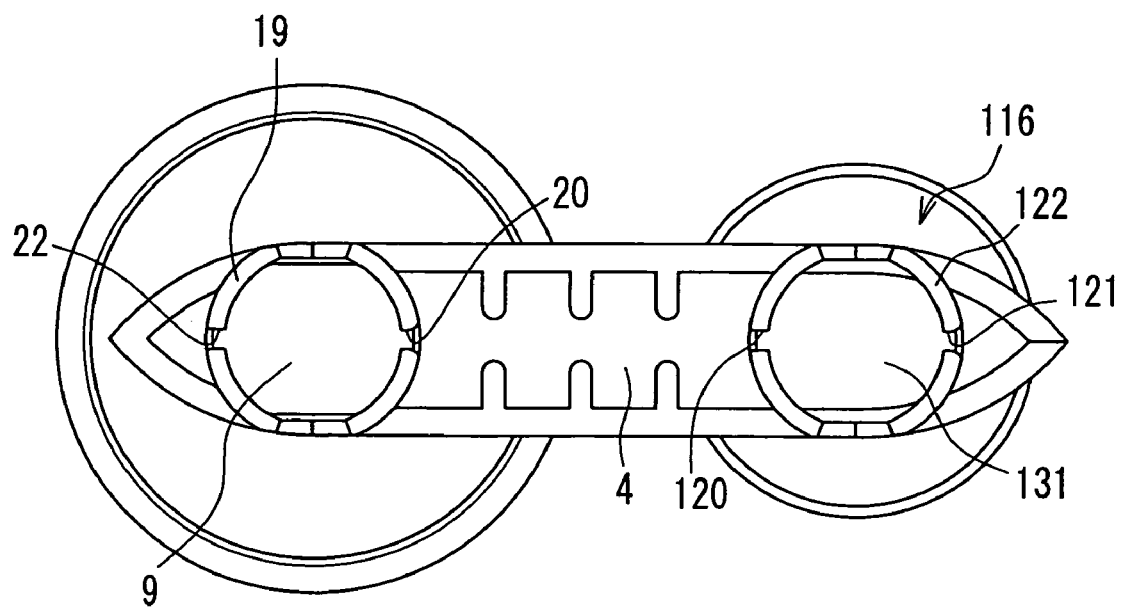
FIG. 19 is an underside view showing another example of the communicating member of the present invention.

Embodiments 1 and 2 described a case in which the barrier member that constitutes the second connection port 16 is provided with a slit or the like that enables the insertion of an object that does not have a sharp tip to prevent accidental penetration. However, the barrier member of the communicating member of the present invention is not limited thereto, and may be a molded article 131 as shown in FIG. 19 that contains, like the plug 9, a material having rubber-like elasticity into which a metal needle, a plastic needle or the like having a sharp tip is stuck.

In this case, it is preferable that a cylindrical member (second approximately cylindrical member) 122 is disposed upright on the plate member 4 on the side opposite the second pedestal of the plate member 4 so that the sheet that constitutes the main container unit does not get broken by a metal needle, a plastic needle or the like. The second approximately cylindrical member 122 is placed, for example, substantially in parallel with the first approximately cylindrical member 19. If the second approximately cylindrical member 122 has a third communicating portion 120 that has an opening on the first opening side, it is easy to move air bubbles that have entered into the inner space of the second connection port 116 out of the second connection port 116, thereby suppressing the retention of air bubbles in the inner space of the second connection port 116, and thus such a configuration is preferable. It is further preferable that the second approximately cylindrical member 122 has a fourth communicating path 121 that is similar to the second communicating portion 22. The third communicating portion 120 and the fourth communicating portion 121 may be formed by, for example, providing a through-hole that penetrates the cylindrical wall of the second approximately cylindrical member 122 in the thickness direction, or may be formed by providing a slit in the cylindrical wall of the second approximately cylindrical member 122 along the longitudinal direction of the second approximately cylindrical member 122.

Figure 20:
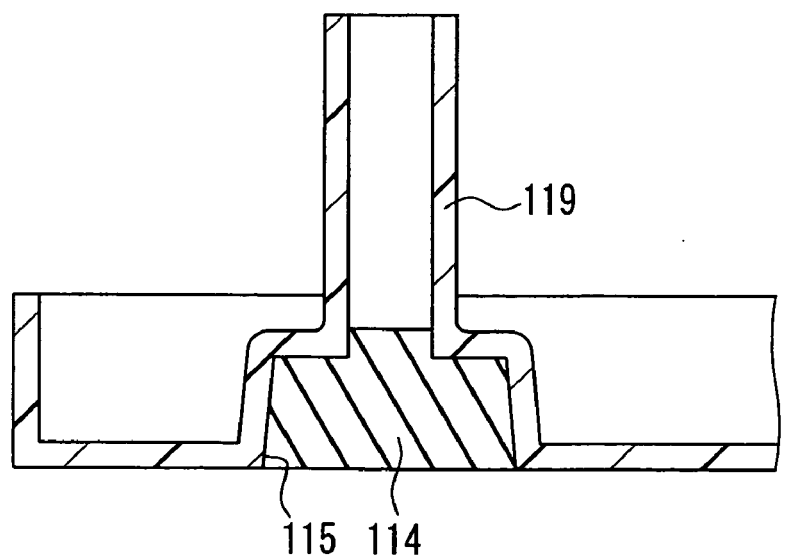
FIG. 20 is an underside view showing yet another example of the communicating member of the present invention.

In Embodiments 1 and 2, with respect to the first connection port 15, the first opening 5 is obturated with the plug 9 by providing the plug 9 in the tip portion of the first pedestal 7 that is disposed upright to the first opening 5. The mode of the obturation of the first opening 5 with the plug 9 is, however, not limited to this. For example, as shown in FIG. 20, the first opening 115 may be obturated by filing with a plug 114 the inner space of the first opening 115 by pressure-fitting or the like. Moreover, part of the plug 114 may enter inside the first approximately cylindrical member 119. In this case, the first pedestal is not necessary.

Industrial Applicability

The communicating member of the present invention can prevent a damage to the main container unit caused by an injection needle or the like inserted into the main container unit through the first connection port and can prevent the retention of air bubbles entered into the inside space of the first connection port, and therefore the communicating member is for use as a component that has a function as a connection port that constitutes a medical container. With a medical container or an infusion preparation tool set in which the communicating member of the present invention is used, it is easy to perform gas-liquid separation in the medical container.

The invention claimed is:

1. A communicating member for a medical container, the communicating member being able to bring into communication the inside and outside of a main container unit composed of a flexible sheet while being fixed to the main container unit, the communicating member comprising:
a plate member having a first opening and a second opening;
a first connection port including the first opening, a plug that obturates the first opening and into which a needle having a sharp tip can be inserted, and a first approximately cylindrical member that is in communication with the first opening;
a second connection port including the second opening and a barrier member that obturates the second opening; and
a continuous wall disposed on the plate member on the first approximately cylindrical member side and disposed upright on the plate member such that the continuous wall encloses the first opening and the second opening when the plate member is viewed from above, wherein the continuous wall can be secured to the sheet by heat sealing after sandwiching the continuous wall with two pieces of the sheet, wherein a part of a peripheral surface of the first approximately cylindrical member constitutes a part of an outer surface of the continuous wall, and an end of the first approximately cylindrical member situated further from the first opening is disposed outside a space enclosed with the continuous wall, the first approximately cylindrical member is provided with a first communicating portion that has an opening on the second opening side of the first approximately cylindrical member, and the first communicating portion is formed by providing a slit in a cylindrical wall of the first approximately cylindrical member along the longitudinal direction of the first approximately cylindrical member.

2. The communicating member according to claim 1, wherein the first connecting port further is provided with a first pedestal that is disposed upright on the plate member so as to be in communication with the first opening, and the plug obturates the first opening by being disposed in a tip portion of the first pedestal.

3. The communicating member according to claim 1, wherein the second connection port further is provided with a second pedestal that is disposed upright on the plate member so as to be in communication with the second opening, and the barrier member obturates the second opening by being disposed in a tip portion of the second pedestal.

4. The communicating member according to claim 1, wherein the first communicating portion is disposed at least in a base portion of the first approximately cylindrical member.

5. The communicating member according to claim 1, wherein the first communicating portion is disposed such that the first communicating portion overlaps part of a line connecting the center of the plug and the center of the barrier member when the communicating member is viewed from above so that the inner space of the first approximately cylindrical member can be seen.

6. The communicating member according to claim 1, wherein the first approximately cylindrical member further is provided with a second communicating portion having an opening on the side of the first approximately cylindrical member further away from the second opening.

7. The communicating member according to claim 1, wherein a plurality of reinforcing ribs are uprightly disposed on the inner surface of the continuous wall and are formed integral with the plate member.

8. The communicating member according to claim 1, wherein the barrier member is a disc-like valve having a slit.

9. The communicating member according to claim 8, wherein in the barrier member, a male luer as defined by ISO594-1 or ISO 594-2 can be inserted into the slit.

10. The communicating member according to claim 1, wherein a covering member that supports the barrier member further is provided, and the periphery of the surface of the barrier member is covered with the covering member.

11. The communicating member according to claim 1, wherein the second connection port further includes a second approximately cylindrical member disposed upright on the plate member so as to be in communication with the second opening.

12. The communicating member according to claim 11, wherein the second approximately cylindrical member is provided with a third communicating portion that has an opening on the first opening side of the second approximately cylindrical member.

13. A medical container comprising:

a main container unit composed of a flexible sheet, and the communicating member according to claim 1 that is fixed to the main container unit and is able to bring the inside and outside of the main container unit into communication, wherein the continuous wall of the communicating member is secured to the sheet by heat sealing after sandwiching the continuous wall with two pieces of the sheet.

14. An infusion preparation tool set comprising the medical container according to claim 13 and a fluid-sending route that is connectable with the second connection port of the communicating member, wherein the fluid-sending route comprises:

a fluid-sending tube, a connecting means that is disposed at one end of the fluid-sending tube, that allows a communicating path that brings the inside of the main container unit of the medical container and the fluid-sending tube into communication to be formed therein, and that can maintain a state of the communicating path being formed, and a needle disposed in the other end of the fluid-sending tube.

15. The infusion preparation tool set according to claim 14, wherein the barrier member of the communicating member is a disc-like valve having a slit, and a tip portion of the connecting means can be inserted into the slit of the barrier member, and the base portion of the connecting means includes a conduit portion that is connected to the fluid-sending tube.

* * * * *